United States Patent [19]

Denny

[11] 4,010,752
[45] Mar. 8, 1977

[54] DISPOSABLE DIAPER HAVING A PUFF BONDED FACING LAYER

[75] Inventor: Thomas Albert Denny, Edison, N.J.

[73] Assignee: Johnson & Johnson, New Brunswick, N.J.

[22] Filed: Jan. 7, 1976

[21] Appl. No.: 647,290

[52] U.S. Cl. .................. 128/284; 128/290 P; 128/290 W

[51] Int. Cl.$^2$ ............ A61F 13/16; B32B 5/16

[58] Field of Search .......... 128/284, 290 R, 290 W, 128/296, 132 D, 290 P

[56] References Cited

UNITED STATES PATENTS

| | | | |
|---|---|---|---|
| 3,095,878 | 7/1963 | Bassett | 128/290 W |
| 3,123,076 | 3/1964 | Griswold | 128/290 W |
| 3,345,243 | 10/1967 | Kalwaites | 428/290 W |
| 3,563,241 | 2/1971 | Evans | 128/284 |
| 3,759,775 | 9/1973 | Shepherd | 428/170 |
| 3,838,694 | 10/1974 | Mesek | 128/287 |
| 3,888,257 | 6/1975 | Cook et al. | 128/296 |
| 3,934,588 | 1/1976 | Mesek | 128/290 W |
| 3,939,836 | 2/1976 | Tunc | 128/284 |

*Primary Examiner*—Aldrich F. Medbery

[57] ABSTRACT

A disposable absorbent bandage such as a diaper has a nonwoven fibrous facing layer which includes side portions flanking a median portion, at least the side portions thereof being impregnated with a volatile liquid containing a binder to secure the interfiber connections to maintain the fiber superstructure and at least the side portions being heated to explosively puff at least the side portions of the web into a gossamer web in which the side portions have a density less than about 0.02 gm./cm.$^3$, and in which the median portion has a density of at least 0.04 gm./cm.$^3$. The differential in fiber densities between the median portion and the side portion results in substantially greater wickability in the median portion than in the side portions and reduces the tendency for leakage at the sides of the diaper.

10 Claims, 9 Drawing Figures

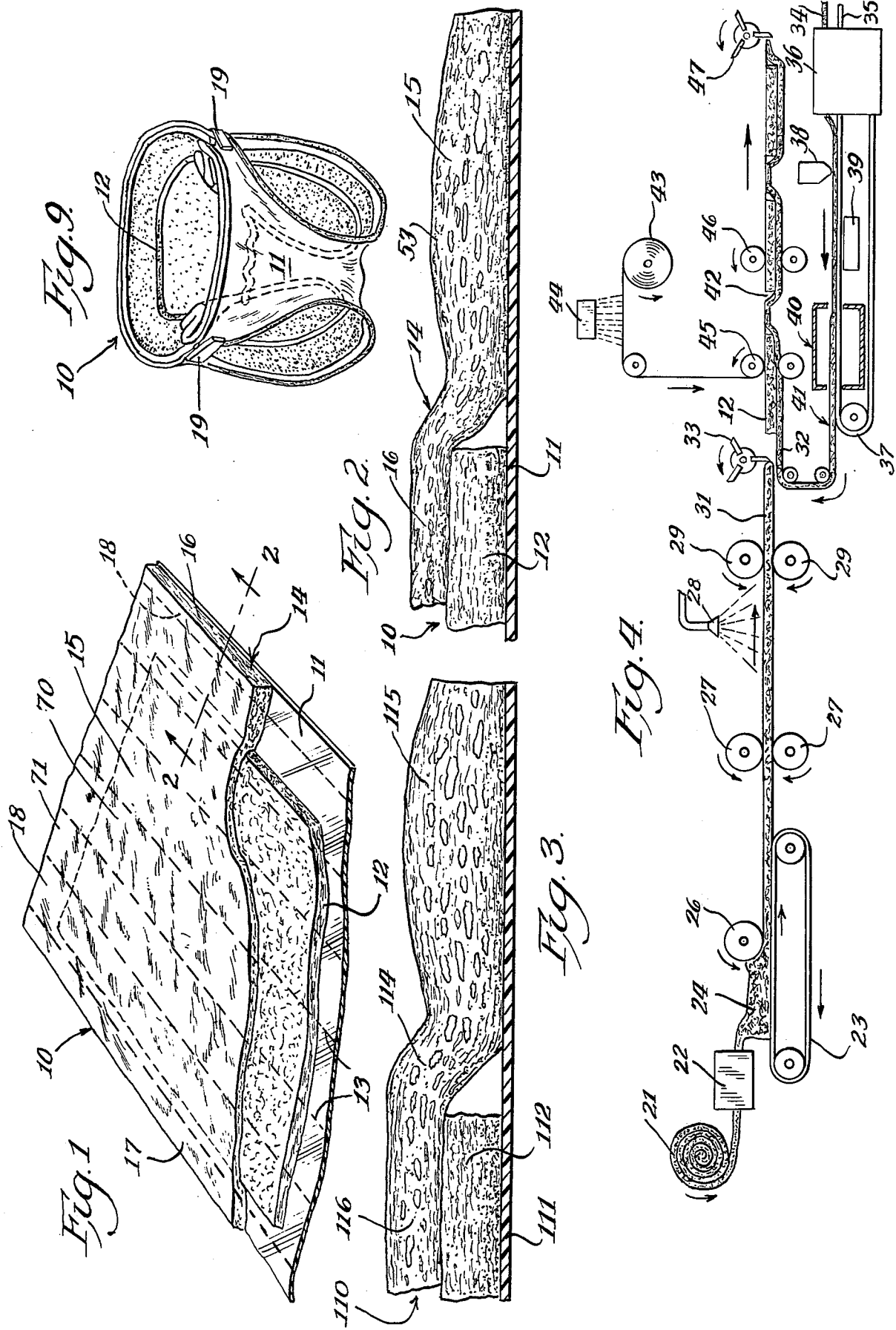

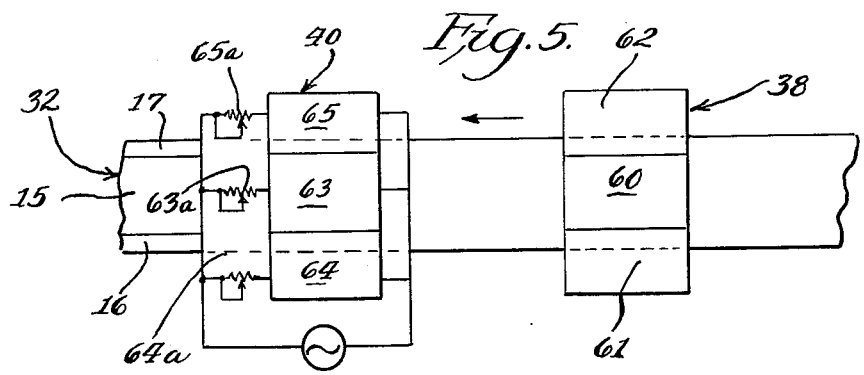
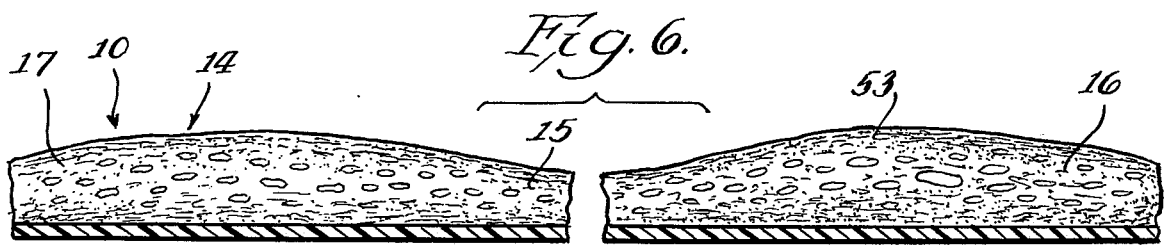
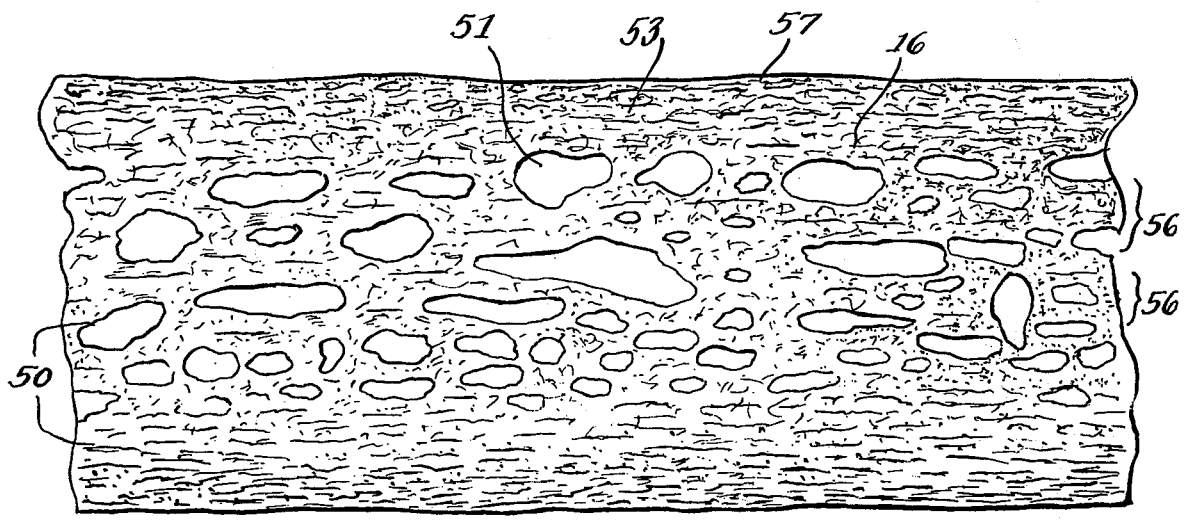
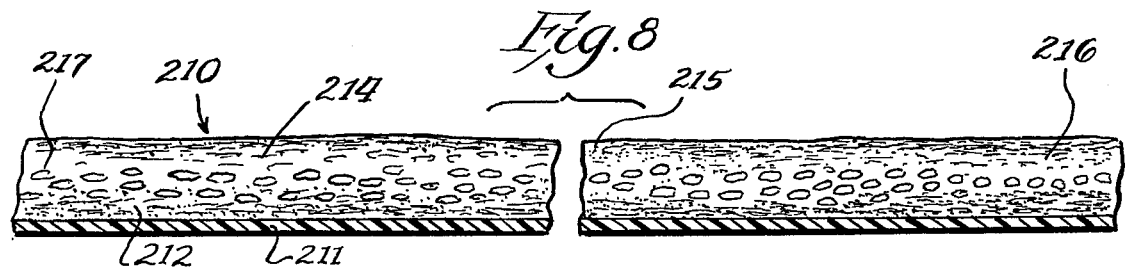

DISPOSABLE DIAPER HAVING A PUFF BONDED FACING LAYER

BACKGROUND OF THE INVENTION

Disposable diapers have met with increased commercial acceptance in recent years primarily because of their convenience, as opposed to cloth diapers, which need to be laundered once soiled. Many different constructions have been proposed and used, and some have met with widespread commercial success.

One of the most serious prior art problems has been the inability to provide a suitable construction that would keep moisture away from the surface of the diaper which comes into contact with the infant's skin and thereby avoid skin irritation and infection. Commonly assigned Mesek et al., U.S. Pat. No. 3,612,055 discloses several diaper constructions that function extremely well in keeping moisture away from an infant's skin while at the same time handling a full volume discharge of urine.

These functions are accomplished by a multilayer diaper comprising, in order, a fibrous facing layer which is to be brought into contact with the infant's skin, a layer of highly porous, loosely compacted cellulosic batt, a paperlike, densified, highly compacted cellulosic fibrous layer integral with the loosely compacted batt and an impervious backing sheet adhered to the densified layer throughout the interface therebetween. The facing layer is of porous construction and its fibers have less wettability for water than the fibers of the loosely compacted batt, resulting in a tendency for liquid to flow from the facing web into the batt. The densified fibrous layer has a smaller average pore size than the loosely compacted batt, resulting in a tendency for liquid to flow preferentially from the batt into the underlying densified layer rather than to other areas of the batt, thus tending to restrict wetting in the batt to an area of moderate size. Liquid flowing into the densified layer tends to spread laterally because of its wicking action and liquid which might pass through the densified layer during discharge (when flow is rapid) is held back by the impervious backing sheet for sufficient time to permit absorption to take place. Liquid in excess of the absorptive capacity of the densified layer is forced back by the impervious layer into the dry portion of the loosely compacted batt, thus utilizing the additional absorptive capacity therein.

The facing layer in the above described diaper is comprised of a mixture of long and short fibers that are held together by a binder having a wetting agent therein which reduces the water repellency of the facing layer, so that urine may readily pass therethrough and into the loosely compacted batt. The binder and wetting agent are uniformly applied across the width and thickness of the facing layer so that the facing layer has uniform functioning properties. While the above type of facing layer has functioned satisfactorily in use, in certain circumstances, particularly when the diaper becomes saturated, there has been a tendency for urine to wick along the facing layer and cause leakage at the sides of the diaper. It has been proposed to obviate this problem by spraying, or otherwise applying, a water-repellent agent on the edges of the facing layer in an effort to prevent urine from wicking outwardly; and commonly assigned U.S. Pat. No. 3,730,184 to Mesek discloses a facing layer which is treated to impart the desired degree of water repellency to the marginal side portions of the facing layer.

SUMMARY OF THE INVENTION

The present invention provides another approach and another solution to the problems of edge leakage in a disposable diaper. In one embodiment it also provides a diaper which can be fitted more closely about the thighs of an infant.

According to the present invention, the marginal side portions of an integral nonwoven web are provided with a controlled and lesser degree of water absorbency than the median portion by expanding and puffing the marginal side portions of the web to a density substantially lower than that of the median portion. Preferably the side portion density is not greater than about 0.02 gm./cm.$^3$, and no more than about half as great as the density of the median portion of the web. Due to a substantially lower fiber density, the side portions of the web have less wickability for liquids than the median portion of the web.

The side portions of the web comprise haphazardly arranged fibers secured together at their junctions by a binder and formed into a cellular structure comprising chambers substantially free of fibers and surrounded by fiber strata. A complete description of webs having an overall structure similar to the structure of the side portions of the web comprising the facing layer of this invention, and of the method of making such webs may be found in Shepherd U.S. Pat. No. 3,759,775, the disclosure of which is hereby incorporated herein by reference.

The median portion of the diaper may be of a noncellular structure or may be a cellular structure having chambers of smaller average size than the chambers in the cellular structure of the side portions.

The method of making a diaper according to the present invention includes the steps of impregnating a nonwoven web of discrete fibers having side portions flanking a median portion with a volatile liquid containing a binder capable of stabilizing the fibers as an interconnected web. The volatile liquid is rapidly vaporized by applying heat substantially to an internal portion of the impregnated web at a rate sufficient to cause expanding vaporized liquid to form liquid membranes within the web and to exert expansive forces on the liquid membranes between the fibers and to thereby separate portions of the web and produce a puffed web portion. The application of the volatile liquid and the heat are correlated to separate and puff the side portions of the web substantially more than the median portion of the web. The binder is set while fibers are in the puffed condition to secure the fibers to one another at interconnections therebetween and thereby to produce a stabilized puffed web with a structure including chambers within the interior of the web surrounded by more dense fiber strata.

One face of the web is brought into face to face contact with one face of an absorbent batt with areas of the web overlapping the edges of the batt, and an opposite face of the batt and the overlapping areas of the web are brought into contact with an impervious flexible layer. The impervious flexible layer is adhered to the opposite face of the batt and to the overlapping areas of the web.

In addition to the differential in wickability between the median and side portions of the web, a further feature of one embodiment of the present invention is the provision of additional bulk at the side edges of a diaper where it serves a useful function. In a typical disposable diaper comprising a facing sheet and a backing sheet of equal dimensions and an absorbent batt of smaller dimension positioned therebetween, the present invention can provide greater thickness at the edges of the diaper where the batt does not extend. Due to this additional thickness, or bulk, at the side edges of the diaper, a better seal is provided at the thighs where tape tabs are used with the present invention.

In an alternate embodiment, the precursor web has a greater thickness in the median portion than in the side portions and, after puffing, the entire web is about equal in thickness at all portions of its width.

BRIEF DESCRIPTION OF THE DRAWINGS

In the drawings:

FIG. 1 is a fragmentary perspective view, partly broken away to show interior detail, of an open diaper in accordance with one embodiment of this invention;

FIG. 2 is an enlarged cross-sectional view of the diaper of FIG. 1 taken along plane 2—2;

FIG. 3 is a cross-sectional view similar to FIG. 2 and illustrating an alternate embodiment of the invention;

FIG. 4 is a simplified schematic view of the production line on which the diaper is made;

FIG. 5 is an enlarged plan view illustrating the liquid applying means and the heating means utilized in the production line of FIG. 4;

FIG. 6 is an enlarged cross-sectional view of the diaper of FIG. 1 wherein side portions of the web have been puffed and the median portion thereof has not been puffed;

FIG. 7 is a cross-sectional view similar to FIG. 6 wherein side portions of the web have been puffed and the median portion thereof has also been puffed but to a lesser extent than the side portions;

FIG. 8 is a cross-sectional view similar to FIG. 6 wherein the entire web is approximately equal in thickness after being puffed; and FIG. 9 is a perspective view of the diaper of FIGS. 1, 2 and 6, shown in the configuration assumed after the diaper is placed on an infant.

DETAILED DESCRIPTION OF THE INVENTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the invention to the embodiments illustrated. The scope of the invention will be pointed out in the appended claims.

Referring to FIG. 1, disposable diaper 10, having a substantially rectangular configuration, is provided with moisture-impermeable backing sheet 11 which forms an outside surface for direction away from an infant and with an absorbent pad or batt 12 situated on backing sheet 11 and attached thereto by means of adhesive beads 13. Moisture-pervious facing sheet or web 14, forming an inside surface for direction toward an infant, overlies batt 12 and is substantially coextensive with backing sheet 11. Batt 12 is smaller in dimension than backing sheet 11 and facing sheet 14, and facing sheet 14 has a median portion 15 overlying batt 12 and side portions 16 and 17 which flank the median portion and overlie marginal portions of backing sheet 11. Facing sheet 14 is similarly attached to backing sheet 11 by adhesive beads 13 which extend beyond the ends of the batt, as shown, and by adhesive beads 18 which run along the side margins of the diaper. Diaper 10 can be provided with adhesive tab fasteners 19 as shown in FIG. 9.

The diaper of this invention may be assembled in equipment such as that schematically shown in FIG. 4. A roll of compacted wood pulp 21 is provided to feed a source of short cellulosic fibers to grinding mill 22 from which a stream of fibers is blown onto belt 23 as a layer 24 weighing between about 2 and about 10 oz./yd.$^2$. The pulpboard normally has a moisture content of 5 to 10 percent by weight, but if it is lower (as from prolonged exposure to a dry atmosphere) the pulpboard may be slightly moistened before grinding in mill 22 to bring its moisture content within the desired range.

Mill 22 grinds the pulpboard into individual short fibers. However, in one preferred embodiment, some of the pulpboard fibers are not completely comminuted and remain joined to other fibers in small clumps, generally smaller than about one-fourth inch across. It has been found that the presence of such small clumps of fibers in the body of batt 12 provides islands of increased tenacity for holding liquid. When an infant's weight on one portion of the batt densifies that portion and tends to concentrate the liquid in the densified portion, the presence of clumps of fibers elsewhere in the batt tends to hold the liquid in place. Preferably from about 2 to about 10 percent by weight of the fibers should be in the form of such clumps.

The air blown layer is passed under compacting roll 26 from which it emerges with enough integrity to sustain itself as a web without the support of belt 23. The web then passes through a pair of calendar rolls 27 for further compression and then under nozzle 28 which deposits a fine spray of moisture on the upper surface of the web. The moistened web then passes between another set of calendar rolls 29 which exert heavy pressure on it to form a skin 31 on its upper surface.

The amount of moisture applied to the web may vary suitably from about 0.005 to about 0.03 cc. of $H_2O/cm.^2$ of web surface, depending on the thickness of the web and the thickness of the paper-like densified skin desired, with lesser amounts of moisture being used for thinner webs and very thin, papery skins and greater amounts for thicker webs and skins of greater thickness.

The amount of pressure applied by rolls 29 may vary from about 5 to about 100 or more lbs./in.$^2$, with the commercially preferable range being from about 10 to about 50 lbs./in.$^2$. In a typical embodiment, the web is sprayed with about 0.0015 cc. of $H_2O/cm.^2$ of web surface and subjected to a pressure of about 40 lbs./in.$^2$ to obtain a densified, coherent papery skin on the surface of the web which has been moistened.

In the absorbent web and in the batts cut therefrom, there are weak hydrogen bonds in the body of the batt providing sufficient strength to maintain the integrity of the batt in ordinary handling, and there are strong hydrogen bonds in the densified layer or skin to increase the cohesive strength of the composite. After the skin is formed, the absorbent web comes into contact with a web of facing material 32 and is supported thereby while being cut by cutter 33 into individual batts 12.

Facing material 32, comprises a nonwoven fibrous web, which is more porous in its marginal side portions than in its median portion and at least a portion of which contains a small amount of binder.

As illustrated in FIG. 4, facing material 32 may be prepared by initially feeding a source 34 of short fibers and a source 35 of textile length fibers to a fiber individualizing and mixing means 36, which separates the fibers from their respective sources, mixes them, and deposits them on a foraminous belt 37. The web forming means may be similar to a Rando-Webber made by the Curlator Co. The web of facing material 32 is thereafter impregnated throughout with an acrylic binder which is dispersible in a vaporizable liquid, such as water, contained in hopper 38 by applying the same to at least side portions 16 and 17 of the top surface of the web and then passing the web over a suction box 39 by virtue of which the binder and water are distributed relatively uniformly throughout the thickness of the web. The vaporizable liquid may flow freely onto web 32 from hopper 38 and suction box 39 may be used to remove excess liquid from the web.

The impregnated web is next passed through a heating means 40 which may comprise one or more dielectric dryers. By virtue of its high loss factor, the water solution rapidly absorbs energy from the heating means, thus causing the liquid in the interior of the web to rapidly heat, vaporize, and expand explosively causing the web to puff as shown at 41 in FIG. 4. As the web of facing material 32 is thus dried, the liquid activated binder sets and the web at 41 is stabilized in its puffed condition.

As shown in schematic plan view in FIG. 5, described below, both hopper 38 and heating means 40 are divided into three separate sections (i.e., a median section and two flanking sections) so that either the amount of liquid applied to each width portion of the web, or the amount of heat applied, or both, can be controlled to provide puffing, or different degrees of puffing, so that the median portion of the web is denser than the side portions.

Polyethylene film 42, which is later cut into a plurality of backing sheets 11, is fed to the assembly from roll 43, lines of adhesive being applied from applicator 44. As described above, the adhesive is applied as parallel lines or beads between the impervious sheet and the densified layer of the batt (or the facing layer in the marginal portion of the diaper). Adhesive may, if desired, be applied as a continuous layer between the polyethylene and the batt, but such application tends to provide excessive stiffness. The adhesive may also be applied in other patterns, such as spaced dots or other forms of so-called "island" bonds, but fairly close overall adhesion between the sheet and the batt is required and no portion of the polyethylene should be more than about 2 inches from a point of adhesion. In the absence of such close overall adhesion, the polyethylene film may be separated from the densified layer to create substantial space in which uncontrollably large amounts of free liquid can accumulate.

After the facing material and polyethylene are brought into contact with opposite faces of the absorbent batts, the assembly is subjected to compression by rolls 45 and 46 to shape the diaper assembly, and the individual diapers are cut off by cutter 47.

If desired, adhesive applicator 44 may be omitted and adhesion between the polyethylene layer and the fibrous layers may be achieved by heat sealing, employing a suitable sealing element in the production line.

The term "vaporizable liquid" contemplates a liquid capable of generating gases at a very rapid rate at temperatures which can be tolerated by the common synthetic and natural fibers. The vaporizable liquid with which portions of web 32 are impregnated is heated rapidly internally of the web to explosively vaporize the same and to puff the previously impregnated portions of the web to an expanded though structurally weak, low density condition. The binder, which has been activated and made adhesive, is then set while the previously impregnated portion of the web is in its puffed or expanded state. This secures the fibers together where they intersect and provides substantial structural integrity.

It is preferred that the liquid have a relatively low surface tension so that it will tend to adhere to the fibers as it partially is vaporized, thus forming discrete, rapidly expanding bubbles of vapor or walls interconnecting the fibers to lift the fibers. It is thought that the bubbles cannot immediately escape from the web where the interfiber membranes extend during the explosive action. Therefore, the gases expand more or less in situ until the bubbles or membranes release the vapor entrapped therein, which then readily escapes through and from the web. The more rapid the vaporization, the greater will be the number of these expanding bubbles thrust into a given interstitial volume within the web at a given moment. It is thought that if the total volume of these expanding bubbles in a given web portion at any moment is greater than the interstitial volume of that web portion, that web portion expands, or becomes puffed in an explosive manner.

Dielectric heating means 40 are preferably used to vaporize the liquid because of the speed of the action and the internal nature of the heating. Dielectric heating occurs generally through the absorption of electrical energy in a dielectric material exposed to a rapidly changing electromagnetic field. Thus, when using dielectric heating means, generally only dielectric substances having a substantial loss factor within the web absorb electrical energy and are heated directly. The amount of heat generated in the fibrous web and the fluids held in the web depends upon the frequency of the electromagnetic field applied to the product, the applied voltage, the effective capacitance of the plates and dielectric material and the power factor or loss factor of the web. The power dissipated in the fibrous web can be calculated in watts from the equation:

$$W = \frac{2 f C E^2 (PF)}{10^6}$$

where
 $f$ = frequency in Hertz
 $C$ = capacitance in microfarads
 $E$ = applied r.m.s. voltage
 $PF$ = power factor.

The dielectric liquid throughout the web will be rapidly heated fairly uniformly according to this equation rather than being heated much more slowly from the outside inwardly as is the case with conventional steam, hot air, or infrared dryers.

As will be described, certain additives will substantially improve the loss factor (lower the power factor) of the fiber web and thus enhance the rapid heating.

These may also be conductive but no detrimental effect results therefrom provided there is an air gap between the heater plates.

If the vaporizable liquid is in fact a solvent for the binder, as the liquid is vaporized and the web dried of the liquid, the binder simultaneously becomes set to interconnect the discrete fibers and stabilize the puffed web. The binder may also be present in the form of thermoplastic fibers or powder, such as plasticized cellulose acetate, and the like, dispersed throughout the web and having an activation temperature at or near the vaporization temperature of the vaporizable liquid. When using a thermoplastic binder and dielectric heating means, the binder activation and deactivation steps may again suitably be combined with the vaporization of the liquid. When the liquid is heated by virtue of the absorption of electric energy from the dielectric dryer and vaporized, the hot vapor within the web is sufficient to cause activation of the thermoplastic fibers or powder. As the web is dried and the conductive liquid is driven off, the loss factor goes down and there is less and less absorption of energy within the web and, therefore, less heating of the web. Thus, the thermoplastic fibers or powder becomes deactivated and bonds the nonthermoplastic fibers together at points of contact with the thermoplastic material.

Although as previously described, the liquid may act as an activating agent for the binder, the primary purpose of the liquid is to provide the vapor to puff the web. When using a volatile liquid and dielectric heating, the degree of puffing may be controlled by varying certain parameters, including the thickness of the web, the loss factor of the liquid, the surface tension or foamability of the liquid, the amount of liquid in the web, and the energy level of the dielectric dryer.

If the liquid used is tap water, in order that most of the vapor produced will be in the form of discrete expanding vapor bubbles or constrained by interfiber membranes, it is necessary to add a foaming or wetting agent to the water. These agents are generally those substances which significantly lower the surface tension of water, such as the polyoxyethylene sorbitan fatty acids esters and sorbitan fatty acid esters. Usually, only small amounts of these agents, on the order of from about 1/10 of 1% to about 1% by weight of the water need be used. However, in the case of a weak foaming agent or if substances which retard foaming are present, 10% or more of the foaming agent by weight of the water may be required. A particularly suitable agent is Triton GR-5, a sulfonated alkyl ester, sold by Rohm & Haas.

The higher the loss factor of the liquid solution, the more rapid is the heating and rate of vaporization. Likewise, the higher the energy level of the dielectric dryer and the higher the web liquid pick-up weight, the more rapid is the rate of vapor-evolution. If the web is very thin, vaporization will occur essentially on the surface of the web, there will be little vapor entrapment by the liquid films and, thus, the vapor will rapidly escape from the web without effecting puffing. Thus, by varying any or all of these factors, the web is puffed to a greater or lesser extent as desired.

In order to heat and vaporize the volatile liquid with commercially available dielectric heaters, having an energy output of about 1 kw./inch width/100 feet (web velocity)/minute, rapidly enough to cause puffing of an impregnated web having a fiber weight of between about 3 and about 19 ounces/yard$^2$ and a thickness of between about 0.05 and about 0.30 inch, the web suitably has a liquid pick-up weight of from about 100% to about 600% and the liquid must have a substantial loss factor. In the case of water, this level of loss factor or power factor may be provided by adding small amounts, on the order of from about 1/100 of 1 to 5% by weight of the weight of the water, of an electrolytic salt, such as ammonium chloride. For example, if tap water is the volatile liquid, the addition of a particular acrylic binder (sold as Hycar 2,600 × 120) in an amount of about 3% solids by weight to the water provides the necessary interfiber stabilization and increases the loss factor substantially. The addition of about 1/10 of 1% by weight of ammonium chloride further increases the loss factor and provides explosive vaporization in a dielectric heater as described. The resistance of an ammonium chloride water solution becomes asymptotic with a salt concentration of about 5% solids by weight and, therefore, there is little advantage in using salt concentrations above this level.

The amount of binder should be selected to provide the desired interfiber bonds while maintaining the absorbent interstices. In the preferred embodiments, the binder comprises between about 4 and 10% of the fabric, by weight on a dry solids basis and with this amount, there is an optimum structural stability and minimum tendency to collapse while still maintaining light weight and high absorbency. Binder add-on in the range of about 1 to about 30% of dry solids by weight can be used. The lower range is acceptable where increased structural collapse under compression is not excessively detrimental, and the upper range is useful where increased rigidity is desired although some increase in cost and weight and some decrease in absorptive capacity may be detected.

Referring now specifically to FIGS. 2, 6 and 7, there are shown magnified transverse cross sections of the puffed facing sheet (web) 14. The total thickness of these webs is actually about ½ inch or less. The puffed web has a cellular or honey-combed appearance throughout most of the stabilized portion and essentially comprises longitudinally and transversely extending haphazardly arranged fiber strata 50 and fiber chambers 51. The fiber chambers 51 separate fiber strata 50 and act essentially as pores within the body of the fabric. Most of the fiber strata 50 have a fiber density approaching that of the unexpanded web, and the fiber chambers 51 have a considerably lower fiber density than the surrounding fiber strata 50. Some portions of the fiber chambers 51 are essentially devoid of fibers, and the chambers are defined by a large number of small fibers secured together at their junctions by a small amount of binder. The chambers defined by the strata are larger than the expected interstitial spaces. The portion 53 of the web 32 near the surfaces of the same, is usually of more nearly uniform and higher density. This is thought to be due to the fact that the bubbles formed in the surface adjacent web portions 53 escape relatively rapidly from the web and do not carry many fibers with them. Thus, little or no puffing occurs in this area.

During heating and drying of webs, most binders which are solvent activated, tend to migrate somewhat toward the surface of the web, especially if the binder pick-up weight is relatively high; and, therefore, the surface adjacent portions 53 of the web may have a higher binder content than the center portions 56 of the web. As a result, a relatively hard "skin" 57 may be formed on the web surfaces. The web portions 56 interposed between the surface adjacent portions 53 tend to be less dense and remain softer and somewhat springy. Thus, a low density high bulk absorbent web may be provided which has a hard enough surface to provide improved scuff resistance, thus minimizing the fluffing off of the surface fibers.

The present invention contemplates selective wickability along various width portions of an integral nonwoven fibrous web. More specifically, it is desired to provide a web including side portions 16 and 17 having an overall density substantially lower than the density of median portion 15. Preferably, the density of the median portion will be at least twice as great as the density of the side portions. Since wickability increases with decreasing interfiber distances, due to increased capillarity with a greater number of fibers per unit volume, the median portion 15 of the web is substantially more absorbent than side portions 16 and 17. Reduced wickability is desired along side portions 16 and 17 of the web in a diaper to minimize any tendency for urine to wick along the facing layer to the marginal side edges thereof.

Various means are contemplated for producing the integral nonwoven webs of the present invention having varying densities therein, with median portion 15 of the web having a substantially greater density than side portions 16 and 17. At least the side portions 16 and 17 of the web are impregnated with a volatile liquid containing a binder capable of stabilizing the fibers in the web as an interconnected web, and the volatile liquid in at least the side portions of the web is rapidly vaporized by applying heat substantially to an internal portion of the web to produce a puffed web portion. The application of the volatile liquid and the heating are correlated to puff only the side portions 16 and 17 of the web, or to puff them substantially more than median portion 15. Only side portions 16 and 17 are puffed in the embodiment of FIGS. 2 and 6; and the entire web is puffed, with side portions 16 and 17 being puffed to a substantially greater extent than median portion 15 in the embodiment of FIG. 3. In the embodiments illustrated in FIGS. 2, 3 and 6, the median portion 15 (115 in FIG. 3) of web 32 has approximately the same fiber weight per unit area as side portions 16 and 17 (116 in FIG. 3), and the side portions are therefore thicker than the median portion. In the embodiment illustrated in FIG. 8, median portion 15 has a higher fiber weight per unit area than side portions 16 and 17 and the entire web is of approximately equal thickness in all width portions after puffing.

As shown in FIG. 5, hopper 38 is divided into median portion 60 and side portions 61 and 62; and heating means 40 comprises a dielectric heater having median portion 63 and side portions 64 and 65. The power to each portion of the dielectric heater is separately controlled by rheostats 63a, 64a and 65a, respectively.

The median portions of the hopper and heater are positioned above the median portion 15 of the web, and the side portions of the hopper and heater are positioned above side portions 16 and 17 of the web. The amount of liquid supplied by the portions of the hopper and the amount of heat produced by each dielectric heater portion are independently adjustable and are variable. If desired, hopper 38 may comprise a plurality of separate hoppers, and heating means 40 may comprise a plurality of separate dielectric heaters.

To puff only the side portions 16 and 17 of the web to produce the web illustrated in FIG. 2, either the volatile liquid is supplied from side portions 61 and 62 of the hopper to only the portions 16 and 17 of the web while the entire web is heated; or the entire web is wetted while only the side portions of the web are heated by side portions 61 and 62 of the dielectric heater. Or, if desired, both the wetting and the dielectric heating may be restricted to the side portions. Where the volatile liquid is supplied to only the side portions of the web, it is desirable to provide binder to the median portion 15 of the web through median portion 60 of the hopper so that the median portion of the web will be a binder stabilized uniform mixture of fibers.

The present invention also contemplates a web which is entirely puffed, but wherein side portions 16 and 17 are expanded substantially more than median portion 15. In the following portion of the description, the same last two digits in each numeral designate similar elements in the various embodiments. Referring to FIGS. 3 and 5, the entire web 132 is impregnated with liquid from hopper 38 and the entire web is heated by dielectric heater 40 to puff the entire web. To puff side portions 116 and 117 of the web substantially more than median portion 115 of the web, a greater quantity of volatile liquid is provided to side portions 116 and 117 of the web from side portions 61 and 62 of the hopper than is provided to median portion 115 of the web from median portion 60 of the hopper. Alternatively, or in addition, more heat is applied to side portions 116 and 117 of the web from side portions 64 and 65 of dielectric heater 40 than is applied to median portion 115 of the web from median portion 63 of the dielectric heater. A greater amount of puffing in side portions 116 and 117 of the web than in median portion 115 of the web can also be accomplished by applying salt to the side portions 116 and 117 of the web through the side portions 61 and 62 of the hopper, and then heating the entire web evenly or applying more heat to the side portions of the web than to the median portion. An ionizing material comprising an electrolytic salt, such as ammonium chloride, increases the heating rate of the liquid in the side portions of the web.

As illustrated in FIG. 8, web 214, after it is puffed, may have approximately the same thickness in side portions 216 and 217 and median portion 215. This is accomplished by starting with a precursor web having a median portion 215 which is thicker than side portions 216 and 217. After the web is puffed, the entire web has about the same thickness due to a substantially greater amount of puffing in side portions 216 and 217 than in median portion 215.

Referring to FIGS. 1, 2 and 5, median portion 15 of web 14 preferably runs lengthwise along diaper 10, and is uniform in construction throughout its length. As shown in FIG. 1, median portion 15 may comprise a central portion 70 and end portions, such as 71, at opposite ends of diaper 10. If desired, end portions 71 are puffed and have a density lower than that of central portion 70 and no greater than about 0.02 gm./cm.$^3$. End portions 71 and side portions 16 and 17 may comprise haphazardly arranged fibers secured together at their junctions by a binder and formed into a cellular structure comprising chambers substantially free of fibers and surrounded by fiber strata.

Webs having end portions as well as side portions of lower density than the central portions may be produced in the same general manner as described above, by restricting the application of the volatile liquid to a hollow, rectangular, "picture-frame" pattern, by restricting the dielectric heating to such a pattern, or both.

The fiber assemblies used in the manufacture of the improved puffed nonwoven fabrics described herein may advantageously use the fiber combination described in detail in commonly assigned U.S. Pat. No. 3,663,348, the various examples and teachings thereof being incorporated herein by reference. The fabric is preferably predominately fibers under about ¼ inch in length, with a minor proportion of long fibers in excess of about ¾ inch in length. A combination of about 70% or more by weight of short fibers under about ¼ inch and about 30% or less long fibers of about ¾ inch or more have proven especially advantageous and economical.

The practice of the invention is not limited to any particular type, length or denier fibers and includes the use of waste fibers, such as chopped threads and the like. Thus, any of the natural fibers such as cotton, linen, hemp, silk, wool, or wood pulp; or synthetic fibers such as rayon, acetate, polyester, acrylic or modacrylic fibers may be used. The method may also be used with fibers of any length, though short fibers are of particular usefulness. Short fibers such as cotton linters or wood pulp are particularly desirable for use in a low cost absorbent product due to their low cost and their ease of handling. In the past, the production of webs of these short fibers have presented the greatest problems with respect to providing low density, high bulk webs. Therefore, it is in producing webs of these short fibers that one may benefit most from the puffing which may be obtained through use of this invention.

The invention has been described with respect to its preferred embodiment in connection with diapers and the preparation of diapers. It will be understood, however, that the fibrous web of this invention may also be used as a facing layer in other absorbent bandages, such as surgical dressings and sanitary napkins, in which a facing layer is in face to face contact with an absorbent batt.

Other modifications and variations will be apparent to those skilled in the art.

I claim:

1. A disposable diaper comprising:
 a moisture-impervious backing sheet,
 an absorbent batt having a first face positioned on one face of said backing sheet,
 and a facing layer having one face in juxtaposition with the other face of the absorbent batt and adhered to said one face of said facing layer,
 said facing layer comprising:
 an integral nonwoven fibrous web having a median portion flanked by side portions, said side portions having an overall density substantially lower than that of at least a portion of said median portion and no greater than about 0.02 grams per cubic centimeter, said side portions comprising haphazardly arranged fibers secured together at their junctions by a binder and formed into a cellular structure comprising chambers substantially free of fibers and surrounded by fiber strata.

2. The diaper of claim 1 wherein said median portion is of a non-cellular structure.

3. The diaper of claim 1 wherein said median portion is of a cellular structure having chambers of smaller average size than the chambers in the cellular structure of said side portions.

4. The diaper of claim 1 wherein said median portion and said side portions have approximately the same fiber weight per unit area and wherein said side portions are thicker than said median portion.

5. The diaper of claim 1 wherein said median portion is of higher fiber weight per unit area than said side portions and is of approximately the same thickness as said side portions.

6. The diaper of claim 1 wherein a rectangular segment of the web of claim 1 has said median portion running lengthwise.

7. The diaper of claim 6 wherein said median portion is of uniform construction throughout its length.

8. The diaper of claim 6 wherein said median portion comprises a central portion and end portions and wherein said end portions have an overall density substantially lower than that of said central portion and no greater than about 0.02 grams per cubic centimeter, said end portions comprising haphazardly arranged portions secured together at their junctions by a binder and formed into a cellular structure comprising chambers substantially free of fibers and surrounded by fiber strata.

9. The diaper of claim 1 wherein the surfaces of said side portions are more dense than the internal portion thereof.

10. An absorbent bandage comprising:
 an absorbent batt having a first face positioned on one face of said backing sheet,
 and a facing layer in juxtaposition with the other face of the absorbent batt and adhered to one face of said facing layer,
 said facing layer comprising:
 an integral nonwoven fibrous web having a median portion flanked by side portions, said side portions having an overall density substantially lower than that of at least a portion of said median portion and no greater than about 0.02 grams per cubic centimeter, said side portions comprising haphazardly arranged fibers secured together at their junctions by a binder and formed into a cellular structure comprising chambers substantially free of fibers and surrounded by fiber strata.

* * * * *